United States Patent [19]
Annen et al.

[11]  4,440,684
[45]  Apr. 3, 1984

[54] PROCESS FOR THE PREPARATION OF 6-METHYL-$\Delta^{4,6}$-3-KETO STEROIDS

[75] Inventors: Klaus Annen; Henry Laurent; Helmut Hofmeister; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 463,702

[22] Filed: Feb. 4, 1983

[30] Foreign Application Priority Data

Feb. 5, 1982 [DE] Fed. Rep. of Germany ....... 3204281

[51] Int. Cl.³ .............................................. C07J 19/00
[52] U.S. Cl. ............................ 260/239.57; 260/397.3; 260/397.4; 260/397.47
[58] Field of Search ............. 260/397.3, 239.57, 397.4, 260/397.47

[56] References Cited
FOREIGN PATENT DOCUMENTS 852683 10/1960 United Kingdom ............. 260/397.4
884544 12/1961 United Kingdom ............. 260/397.4

Primary Examiner—Elbert L. Roberts
Attorney, Agent, or Firm—Millen & White

[57] ABSTRACT

A process for preparing 6-methyl-$\Delta^{4,6}$-3-keto steroids of the formula

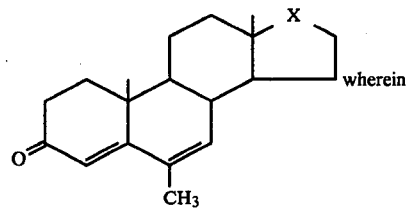

wherein X is 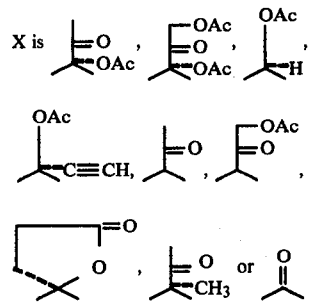

comprises reacting a corresponding $\Delta^4$-3-keto steroid with methoxymethyl acetate ($CH_3$—O—$CH_2$—OAc) in an inert solvent at temperatures above room temperature in the presence of an alkali metal acetate.

23 Claims, No Drawings

PROCESS FOR THE PREPARATION OF 6-METHYL-Δ$^{4,6}$-3-KETO STEROIDS

BACKGROUND INFORMATION

The present invention relates to a method for preparing 6-methyl steroids.

The 6-methyl steroids producible according to this invention, especially those of the pregnane series, are known pharmaceuticals. Since the presence of the 6-methyl group frequently causes a considerable rise in efficacy in steroidal progestogens and corticoids, numerous efforts have been made in the past to provide methods of introducing this methyl group.

Thus, for example, megestrol acetate (17α-acetoxy-6-methyl-4,6-pregnadiene-3,20-dione) is utilized for the treatment of inoperable, metastasizing endometrial carcinoma, and medrogestone (6,17-dimethyl-4,6-pregnadiene-3,20-dione) is used for the treatment of menstrual disorders and premenstrual tension conditions.

Megestrol acetate is prepared according to a synthesis by Djerassi and Ringold [H. H. Ringold et al., J. Amer. Chem. Soc. 81: 3712 (1959)] in a multistage procedure by ketalizing 3β-acetoxy-17α-hydroxy-5-pregnen-20-one, epoxidizing the thus-obtained 20-ketal on the Δ$^5$-double bond, and reacting the resultant 5,6α-epoxy-20-ethylenedioxy steroid with a methylmagnesium halide to form 6β-methyl-5α-hydroxyketal, while also splitting off the 3α-acetoxy group during this step. After ketal cleavage and subsequent oxidation, 5α,17α-dihydroxy-6β-methyl-3,20-diketopregnane is obtained yielding 6α-methyl-17α-hydroxyprogesterone while splitting off water and with inversion of the 6-methyl group. Acetylation on the C-17 leads to 6α-methyl-17α-acetoxyprogesterone, and subsequent dehydrogenation results in the desired Δ$^{4,6}$-dienone.

A newer synthesis [F. Schneider et al., Helv. Chim. Acta 56: 2396 (1973)] starts with 17α-acetoxyprogesterone, which is first blocked in the 3-position by a pyrrolidino group and then reacted with formaldehyde to form 6β-hydroxymethylene-17α-acetoxyprogesterone. By splitting off water, the 6-exomethylene compound is obtained; the latter is isomerized with palladium/carbon/cyclohexane to form the desired 6-methyl-Δ$^{4,6}$-compound.

The synthesis described by Petrow or Kadamski [V. Petrow et al., Tetrahedron 21: 1619 (1965); ibid. 25: 1165 (1968); or G. M. Kadamski et al., Khim. Farm. Zh. 1979 (6) 63] proceeds likewise in a similar way. The starting compound here is also 17α-acetoxyhydroxyprogesterone which, after 3-enolizing with dimethylformamide in a Vilsmeier reaction, reacts to form the Schiff base. Hydrolysis yields the 6-formyl compound and, after reduction, the 6-hydroxymethylene compound. By means of a further hydrolysis, the 6-exomethylene compound is then obtained which is again isomerized to the desired 6-methyl-4,6-dienone.

All of these syntheses have the drawback in common that they proceed over a number of stages, thus naturally reducing the final yield of the desired 6-methyl-4,6-dienone compound.

SUMMARY OF THE INVENTION

Accordingly, it is an object of the present invention to provide a process for preparing such steroids which requires fewer stages and is otherwise advantageous.

Upon further study of the specification and appended claims, further objects and advantages of this invention will become apparent to those skilled in the art.

It has now been found surprisingly that the synthesis can be accomplished in a single reaction stage in accordance with this invention by provision of a process for preparing 6-methyl-Δ$^{4,6}$-3-keto steroids of the formula

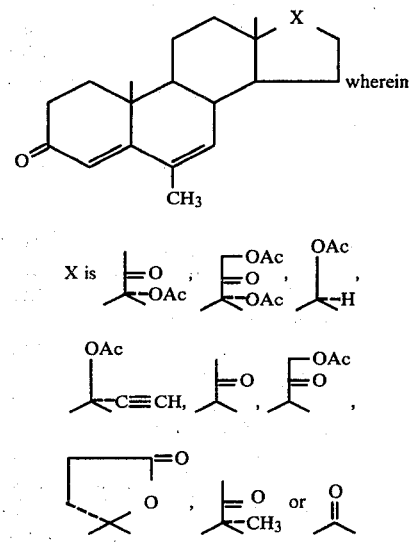

wherein

X is =O, $\begin{matrix}-OAc\\-OAc\end{matrix}$, $\begin{matrix}-OAc\\-H\end{matrix}$, $\begin{matrix}OAc\\-C\equiv CH,\end{matrix}$ =O, $\begin{matrix}-OAc\\-O\end{matrix}$, $\begin{matrix}=O\\O\end{matrix}$, $\begin{matrix}-O\\-CH_3\end{matrix}$ or $\begin{matrix}O\\\parallel\end{matrix}$ comprising reacting a corresponding Δ$^4$-3-keto steroid with methoxymethyl acetate (CH$_3$—O—CH$_2$—OAc) in an inert solvent at temperatures above room temperature in the presence of an alkali metal acetate.

DETAILED DISCUSSION

In that invention, the 3-keto-Δ$^4$-steroid is reacted, in the presence of an alkali metal acetate, with methoxymethyl acetate (CH$_3$O—CH$_2$—OAc) in an inert solvent at temperatures above room temperature, to form the 6-methyl-Δ$^{4,6}$-steroid in one reaction step.

Examples of suitable inert reaction compatible solvents include aliphatic hydrocarbons, e.g., petroleum ether, hexane, and cyclohexane; halogenated hydrocarbons, e.g., methylene chloride, chloroform, carbon tetrachloride, and 1,2-dichloroethane; as well as straight-chain and cyclic ethers, e.g., diisopropyl ether, tetrahydrofuran, and dioxane. The solvents can be utilized singly or also as mixtures with one another.

The reactant methoxymethyl acetate, is usually provided in an amount of 10–100 molar equivalents, preferably about 30 molar equivalents, based on the amount of the starting material steroid. The amount of alkali metal acetate employed is actually uncritical. Suitably, this compound is used in a quantity of 0.5–2, usually about 1, molar equivalents, based on the amount of the steroid. Only sodium acetate and potassium acetate are practically industrially suitable, but the other alkali metal acetates could be used.

The reaction can be conducted without any special measures regarding the surrounding atmosphere. However, it is also possible to use a protective gas atmosphere.

The reaction is conducted with heating. To accomplish this, a bath can be used to maintain a temperature above room temperature (i.e., above about 25° C.), usually at least at 40° C. The practical upper limit lies at the boiling point of the reaction mixture. A temperature range of 50°–90° C. is preferred. Usual reaction times are 2–5 hours. The reaction is preferably run under anhydrous conditions.

An important advantage of the process of this invention is that the corresponding 3-keto-6-methyl-$\Delta^{4,6}$-steroid product is obtained from a 3-keto-$\Delta^4$-steroid directly, in a single reaction step.

All of the starting material $\Delta^4$-3-keto steroids used in the process of this invention are known and are readily preparable using conventional methods from known starting materials. See, e.g., L. Fieser & M. Fieser, Steroids, Reinhold Publ. Corp., N.Y. 1959 or D. Lednicer & L. A. Mitscher, The Organic Chemistry of Drug Synthesis, J. Wiley & Sons, N.Y. 1977.

All of the 6-methyl steroids produced by the process of this invention are known compounds of known pharmacological activity, e.g., as discussed above. See, e.g., Tetrahedron Letters, 21 (1965) p. 1619; J. Org. Chem., 26 (1961) p. 3077; Gazz. Chim. Ital., 92 (1962) p. 547; Ann. Chim., 51 (1961) 912; German Patent No. 1,229,523 and J.C.S. 1960, p. 2828.

Contemplated equivalents of methoxymethyl acetate for use as a reactant in the process of this invention include the homologous alkoxy methyl acylates of the general formula R'—COO—CH$_2$—O—R, wherein R and R' mean lower alkyl other than methyl, which can easily be prepared from the corresponding carbonic acid anhydrides and the acetals of formaldehyde according to the procedure of W. B. Hughes et al., J.A.C.S., 76 (1954) p. 5161. The methoxymethyl acetate is the preferred reactant because the higher homologues are more reactive at elevated temperatures resulting in an increasing amount of products of decomposition.

Contemplated equivalents of the alkali metal acetates for use as a reactant in the process of this invention include the alcaline earth metal acetates, e.g., calcium acetate.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A suspension of 0.5 g of sodium acetate in 60 ml of anhydrous chloroform and 2 ml of distilled phosphorus oxychloride is refluxed under agitation for 30 minutes at a bath temperature of 70° C. After adding 15 ml of methoxymethyl acetate and 2.0 g of 17α-acetoxy-4-pregnene-3,20-dione, the reaction solution is further stirred for 5 hours at 70° C. Subsequently such an amount of a saturated soda solution is added dropwise at room temperature that the aqueous phase remains alkaline. The organic phase is separated, washed with water, and dried over sodium sulfate. After concentration, the crude product is purified on 100 g of silica gel with a hexane-ethyl acetate gradient (0–50% ethyl acetate), thus isolating 1.26 g of 17α-acetoxy-6-methyl-4,6-pregnadiene-3,20-dione, mp 217°–219° C.

EXAMPLE 2

Under argon, a suspension of 0.5 g of sodium acetate in 60 ml of anhydrous chloroform, 2 ml of distilled phosphorus oxychloride, and 15 ml of methoxymethyl acetate is agitated for 30 minutes at a bath temperature of 60° C. After adding 2.0 g of 17α,21-diacetoxy-4-pregnene-3,20-dione, the mixture is further stirred for 3 hours at 70° C. and worked up analogously to Example 1. The dark crude product is purified on 200 g of silica gel with a hexane-ethyl acetate gradient (0–40% ethyl acetate), yielding 1.15 g of 17α,21-diacetoxy-6-methyl-4,6-pregnadiene-3,20-dione, mp 213°–215° C.

EXAMPLE 3

Analogously to Example 2, the following compounds are prepared from the corresponding 3-keto-$\Delta^4$-steroids:

| Compound | Solvent | Bath Temperature (°C.) | Yield (%) | MP(°C.) |
| --- | --- | --- | --- | --- |
| 6-Methyl-17α-pregna-4,6-diene-21,17-carbolactone | Chlf. | 70 | 54 | 195–197 |
| 17β-Acetoxy-6-methyl-4,6-androstadien-3-one | MeCl$_2$ | 45 | 51 | 173–175 |
| 6,17α-Dimethyl-4,6-pregnadiene-3,20-dione | Chlf. | 60 | 43 | 143–145 |
| 21-Acetoxy-6-methyl-4,6-pregnadiene-3,20-dione | Chlf. | 65 | 38 | 113–115 |
| 17β-Acetoxy-17α-ethynyl-6-methyl-4,6-androstadien-3-one | Chlf. | 60 | 24 | 149–151 |
| 6-Methyl-4,6-pregnadiene-3,20-dione | Dioxane | 70 | 27 | 152–154 |
| 6-Methyl-4,6-androstadiene-3,17-dione | 1,2-Dichloroethane | 65 | 22 | 162–164 |

Chlf. = chloroform
MeCl$_2$ = methylene chloride

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 6-methyl-$\Delta^{4,6}$-3-keto steroid of the formula

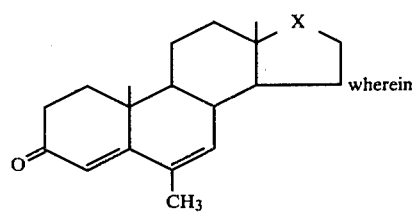

wherein

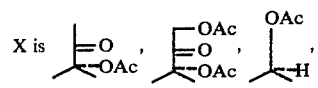

-continued

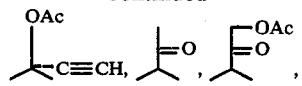, 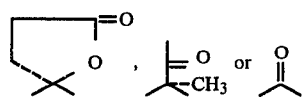,

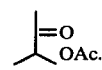

comprising
reacting, in a single stage, a corresponding $\Delta^4$-3-keto steroid, in the presence of an alkali metal acetate, with methoxymethyl acetate in an inert solvent at a temperature above room temperature.

2. A process of claim 1 wherein the reaction is conducted at a temperature of from 40° C. up to the boiling temperature of the reaction mixture.

3. A process of claim 1 wherein the amount of methoxymethyl acetate is 1–100 molar equivalents, based on the amount of $\Delta^4$-3-keto steroid.

4. A process of claim 1 wherein the amount of alkali metal acetate is 0.5–2 molar equivalents, based on the amount of $\Delta^4$-3-keto steroid.

5. A process of claim 1 wherein the reaction is conducted at a temperature of 50°–90° C.

6. A process of claim 1 wherein the alkali metal acetate is sodium acetate or potassium acetate.

7. A process of claim 2 wherein the alkali metal acetate is sodium acetate of potassium acetate.

8. A process of claim 7 wherein the reaction is conducted at a temperature of from 40° C. up to the boiling temperature of the reaction mixture.

9. A process of claim 8 wherein the amount of methoxy-methyl acetate is 1–100 molar equivalents, based on the amount of $\Delta^4$-3-keto steroid.

10. A process of claim 9 wherein the reaction is conducted at a temperature of 50°–90° C.

11. A process of claim 3 wherein the alkali metal acetate is sodium acetate or potassium acetate.

12. A process of claim 5 wherein the alkali metal acetate is sodium acetate or potassium acetate.

13. A process of claim 1 which is conducted under a protective gas atmosphere.

14. A process of claim 1 wherein X is

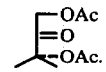

15. A process of claim 1 wherein X is

16. A process of claim 1 wherein X is

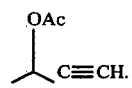

17. A process of claim 1 wherein X is

18. A process of claim 1 wherein X is

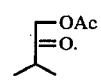

19. A process of claim 1 wherein X is

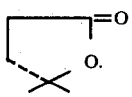

20. A process of claim 1 wherein X is

21. A process of claim 1 wherein X is

22. A process of claim 1 wherein X is

23. A process of claim 1 which is conducted under anhydrous conditions.

* * * * *